United States Patent [19]

Akhavi

[11] 4,240,427
[45] Dec. 23, 1980

[54] NEEDLE WITH PROTECTOR

[75] Inventor: David S. Akhavi, Los Angeles, Calif.

[73] Assignee: American Hospital Supply Corporation, Evanston, Ill.

[21] Appl. No.: 953,610

[22] Filed: Oct. 23, 1978

[51] Int. Cl.² ............................................. A61M 5/00
[52] U.S. Cl. ................................. 128/218 N; 128/221
[58] Field of Search ............... 128/218 R, 218 N, 221, 128/215, 216; 206/365

[56] References Cited

U.S. PATENT DOCUMENTS

| 2,677,373 | 5/1954 | Barradas | 128/216 |
|---|---|---|---|
| 2,953,243 | 9/1960 | Roehr | 206/365 |
| 3,112,747 | 12/1963 | Cowley | 128/218 |
| 3,333,682 | 8/1967 | Burke | 206/365 |
| 3,390,759 | 7/1968 | Vanderbeck | 128/221 X |
| 3,721,241 | 3/1973 | Klohr et al. | 128/221 |

Primary Examiner—John D. Yasko
Attorney, Agent, or Firm—Larry N. Barger

[57] ABSTRACT

An interfitting rib structure on a hypodermic needle and its protector which have beveled ends to rotationally shift the needle and protector into proper alignment during high speed assembly.

8 Claims, 4 Drawing Figures

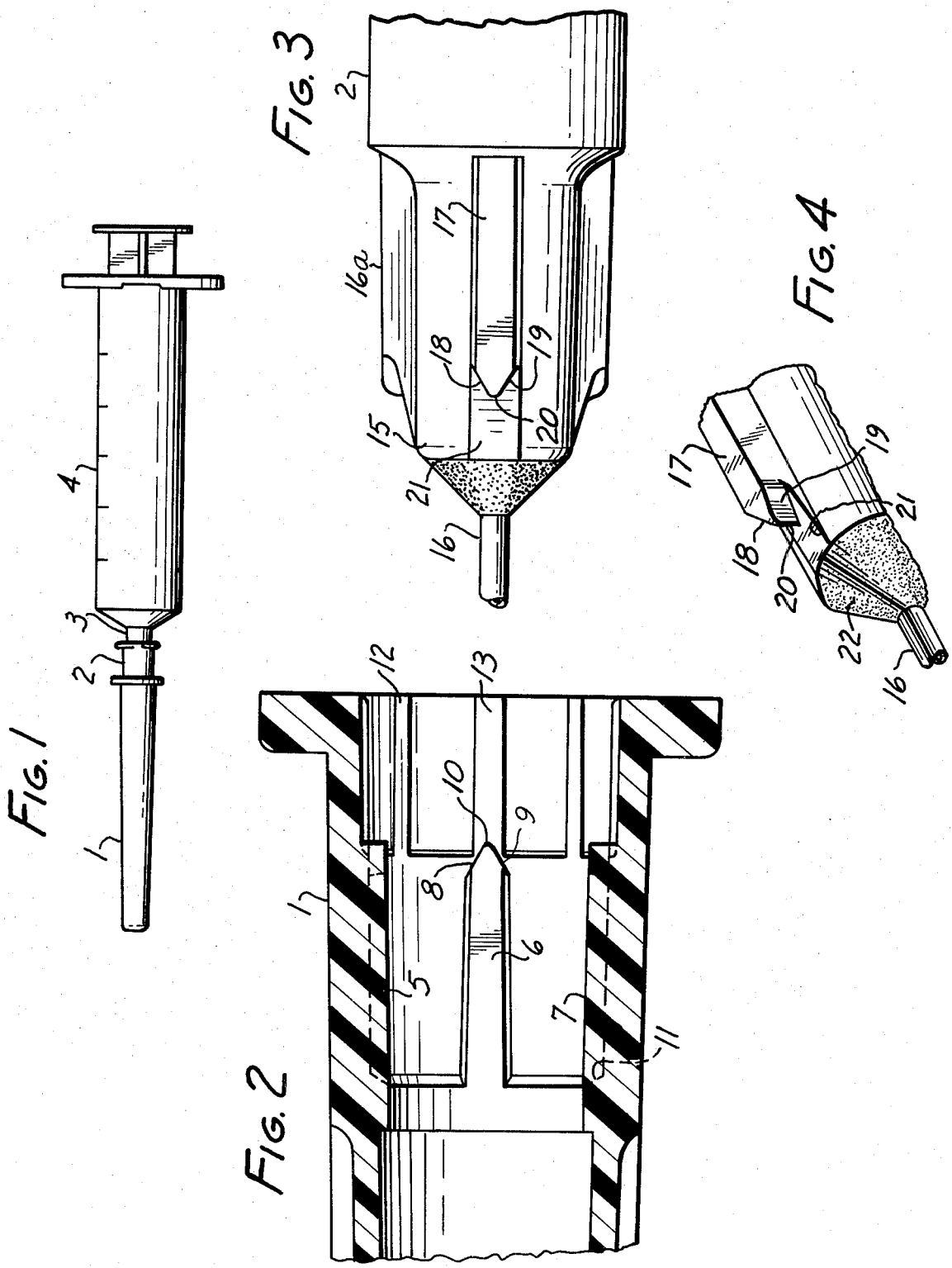

NEEDLE WITH PROTECTOR

BACKGROUND

It is known to mount hollow protectors on the hub of hypodermic needles as illustrated by U.S. Pat. Nos. 3,390,759; 3,333,682; and 2,677,373. These patents also describe an interfitting rib structure between the protector and needle hub forming a "wrench" effect to rotationally lock the needle to the protector. Thus, a nurse or physician can twistingly wedge the needle hub onto a syringe adapter by twisting the protector without manually touching the protector encased needle.

When the protector is mounted on the needle hub, it must have a proper rotational orientation to the needle hub in order for the interfitting ribs to mesh. This is no problem with manual assembly because the operator can simply twist the protector until the protector ribs fall into place between ribs on the needle hub.

In recent years disposable plastic syringes, which are used for a single injection and then discarded, have come into very wide use. In order to keep the cost of such syringes sufficiently low; i.e., only a few cents, very high speed assembly machines are required. Such machines have a certain degree of vibration that tends to help jostle the syringes and needles into proper alignment. However, sometimes end surfaces on the protector and needle ribs will come into an end to end abutting relationship preventing assembly. When this happens, the assembly machine jams, requiring the efforts of an operator to manually unjam the machine. Such jamming is costly in the manufacture of disposable hypodermic syringes.

SUMMARY OF THE INVENTION

The above problems of jamming in high speed production machinery have been overcome by including rotational shifting surfaces (such as beveled) at the ends of the ribs in the protectors and on the needle hub. Such bevels substantially reduce the area of the rib ends which could come into abutting relationship, making it extremely rare for such to occur during assembly. Additional structure of lead-in ramps to the beveled ends of the hub ribs help center the needle hub in the protector cavity during assembly.

THE DRAWINGS

FIG. 1 is a side elevational view of a protector mounted on a hypodermic needle, which is in turn connected to a syringe;

FIG. 2 is an enlarged fragmentary sectional view of a protector showing its internal rib structure;

FIG. 3 is an enlarged fragmentary view of the needle hub showing its external rib structure; and FIG. 4 is a prospective view of a forward end of a hub rib.

DETAILED DESCRIPTION

FIG. 1 shows a hollow needle protector 1 wedgingly mounted on a needle hub 2, which is in turn wedgingly fitted on a tapered adapter 3 of a syringe 4. As previously mentioned, an interconnecting wrenching structure between protector 1 and hub 2 permit the operator to grasp the protector 1 and twistingly assemble or disassemble the needle to tapered adapter 3.

FIG. 2 shows the internal rear section of the protector which includes a series of ribs, such as 5, 6, and 7. This protector would have four ribs, but any number of ribs could be used. A rearward end portion, as shown in rib 6, includes beveled surfaces 8 and 9, causing a rearwardmost end of rib 6 to have a very narrow transverse area. At a forward end of a rib are bottoming shoulders, such as 11, which can abut the needle hub's ribs to limit how deep the hub can be inserted into the protector. For gas sterilization, a series of longitudinal vent ribs, such as 12 and 13, could be used.

The hub 2 in FIG. 3 has a forward section 15 which is joined to a cannula 16 by an epoxy 22. This forward section 15 of the hub has a series of upstanding longitudinal ribs 16a and 17. This hub could be separately formed and attached to a syringe barrel as shown, or could be an integral hub portion of the syringe barrel. A forward end of rib 17 includes beveled surfaces 18 and 19 forming a very narrow forward end 20 of rib 17. Thus, during assembly it is highly unlikely that narrow rearward end 10 of rib 6 in the protector would abuttingly engage the narrow forward end 20 of hub rib 17 and cause the assembly machine to jam.

A prospective view of rib 17 in FIG. 4 shows more detail of this structure. The needle hub also preferably includes a tapered lead-in ramp 21 to help center the hub and the protector. A forward section of lead-in ramp 21 blends with a generally conical shaped epoxy bond 22.

In the foregoing description, double beveled surfaces on the tip of the ribs have been described. It is also within the scope of the invention to use a single bevel in which a narrow tip is adjacent one side of the rib. Also, a generally semi-circular tip end of the ribs would substantially decrease their chance of end to end abutting contact. The important thing is to substantially reduce the transverse area of the rib at its tip from that of the rib body to minimize jamming during assembly, by automatic rotational shifting of the hub and protector during axial assembly.

In the foregoing description, a specific example has been used to describe the invention. However, it is understood by those skilled in the art that certain modifications can be made to this example without departing from the spirit and scope of the invention.

I claim:

1. A needle hub and protector with interfitting ribs, wherein the improvement comprises: at least one rib on the needle hub having a forward end with a rotational shifting surface; and at least one rib on the protector having a rearward end with a rotational shifting surface, whereby said surfaces can engage each other during axial sliding of the needle hub into the protector and automatically prevent rib abutment jamming during assembly.

2. A needle hub and protector as set forth in claim 1, wherein the surfaces are beveled.

3. A needle hub and protector as set forth in claim 2, wherein the surfaces each include two side bevels.

4. A needle hub and protector as set forth in claim 1, wherein at least one surface has a lead-in ramp for laterally positioning the needle hub in the protector.

5. A needle hub and protector as set forth in claim 4, wherein the lead-in ramp is on the needle hub.

6. A needle hub and protector as set forth in claim 1, wherein the needle hub and protector each have a series of beveled rotational shifting surfaces.

7. A needle hub with an external rib for interfitting with a protector or the like, wherein the improvement comprises: said external rib has a forward end with a beveled rotational shifting surface, whereby said beveled surface is adapted to automatically prevent rib abutment jamming during axial assembly of the needle hub into a protector with an internal rib.

8. A protector with an internal rib for interfitting with a needle hub or the like, wherein the improvement comprises: said internal rib has a rearward end with a beveled rotational shifting surface, whereby said beveled surface is adapted to automatically prevent rib abutment jamming during axial assembly of a needle hub with an external rib into such protector.

* * * * *